(12) United States Patent
Rickert et al.

(10) Patent No.: US 6,437,045 B1
(45) Date of Patent: Aug. 20, 2002

(54) POWDER COATING OF CARBOXYL POLYESTER OR (POLY)METHACRYLATE AND CYCLOALIPHATIC POLYEPOXIDE

(75) Inventors: Christoph Rickert, Reinach (CH); François Turpin, Huningue; Jacques Francois, Saint Louis, both of (FR); Mireille Tena, Rheinfelden (CH)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/697,331

(22) Filed: Oct. 25, 2000

(30) Foreign Application Priority Data

Nov. 10, 1999 (CH) .............................. 20561-99

(51) Int. Cl.[7] .......................... C08L 33/02; C08L 63/00
(52) U.S. Cl. ...................... 525/119; 525/438; 549/368; 549/453; 549/525; 549/561
(58) Field of Search ................. 525/438, 119; 549/368, 453, 525, 561

(56) References Cited

U.S. PATENT DOCUMENTS

| | | | |
|---|---|---|---|
| 3,397,254 A | | 8/1968 | Wynstra et al. ............. 260/835 |
| 3,758,633 A | * | 9/1973 | Labana et al. .............. 525/199 |
| 5,294,683 A | | 3/1994 | Cotting et al. .............. 525/524 |
| 5,770,268 A | | 6/1998 | Kuo et al. .................. 427/386 |
| 5,880,223 A | * | 3/1999 | Shah et al. ................. 525/438 |
| 6,099,899 A | * | 8/2000 | Briggs et al. ............... 427/203 |
| 6,165,558 A | | 12/2000 | Schneider .................. 427/386 |

FOREIGN PATENT DOCUMENTS

| | | | |
|---|---|---|---|
| EP | 0600546 | | 6/1994 |
| EP | 0770605 | | 5/1997 |
| EP | 0770650 | | 5/1997 |
| GB | 870696 | * | 6/1961 |
| JP | 11-100378 A | * | 4/1999 |
| SU | 1792956 A1 | * | 2/1993 |
| WO | 94/14906 | | 7/1994 |

OTHER PUBLICATIONS

Batog et al., "Polymer materials based on alicyclic tri– and tetraepoxides," Plast. Massy. (1979), vol. 10, pp. 9–10.*
Derwent Abstract 1994–133020 [16] for SU 1792956 (1993).
A. E. Batog et al., USSR., Plast. Massy (1979), (10), pp. 9–10 (English abstr. included).
Ullmann's Encyclopedia of Industrial Chemistry, 5th, Completely Revised Edition, vol. A9, (1987), pp. 558–559.
Abstract for EP 0770605 (1997).
Abstract for EP 0770650 (1997).
Abstract for JP 53140395 (1978).

* cited by examiner

Primary Examiner—Robert E. L. Sellers
(74) Attorney, Agent, or Firm—Lyon & Lyon LLP; James H. Shalek; Kristin H. Neuman

(57) ABSTRACT

Powder coating compositions comprise a binder selected from carboxyl-group-containing polyesters, carboxyl-group-containing poly(meth)acrylates and mixtures of the said substances, and one or more epoxy compounds, wherein the epoxy compounds comprise at least one compound of formula (I) that is solid at 25° C.:

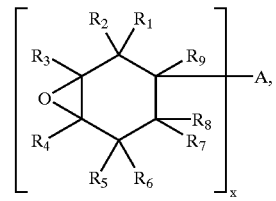

(I)

wherein
A corresponds to a group of formula (II), (III), (IV) or (VI):

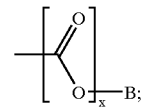

(II)

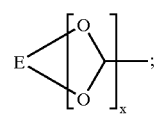

(III)

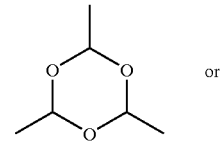

(IV)

or

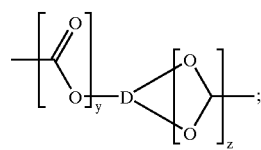
(VI)

in which
B is an x-valent organic radical that is derived from a polyol having x or more hydroxyl groups by the removal of x hydroxyl groups;
E is a (2x)-valent organic radical that is derived from a polyol having (2x) or more hydroxyl groups by the removal of (2x) hydroxyl groups; and
D is a (y+2z)-valent radical that is derived from a polyol having (y+2z) or more hydroxyl groups by the removal of (y+2z) hydroxyl groups;
$R_1$ and $R_5$ are each independently of the other hydrogen, halogen, $C_1$–$C_4$alkyl or $C_1$–$C_4$alkoxy or are together a methylene group; and
$R_2$, $R_3$, $R_4$, $R_6$, $R_7$, $R_8$ and $R_9$ are each independently of the others hydrogen, halogen, $C_1$–$C_4$alkyl or $C_1$–$C_4$alkoxy;
x is an integer of at least 3;
y is an integer from 1 to (x–1) and
z is (x–y).

10 Claims, No Drawings

POWDER COATING OF CARBOXYL POLYESTER OR (POLY)METHACRYLATE AND CYCLOALIPHATIC POLYEPOXIDE

The invention relates to a powder coating composition comprising a binder selected from carboxyl-group-containing polyesters, carboxyl-group-containing poly (meth)acrylates and mixtures of the said substances, and one or more epoxy compounds as thermal hardeners, and also to a preferred preparation process for one type of the epoxy compounds that are to be used.

Powder coating compositions as referred to at the outset are used in a wide variety of forms. Triglycidyl isocyanurate (TGIC) has been successful as an epoxy hardener in such compositions, especially for external paints, which must have a high weather resistance. Its solid consistency, inter alia, has resulted in TGIC being considered today as the standard hardener for powder coating compositions based on carboxyl-group-containing polyesters as binders (see, e.g. Ullmann's Encyclopedia of Industrial Chemistry, 5th Ed., Vol A9, p. 559) and on carboxyl-group-containing poly (meth)acrylates (see, e.g., Johnson Wax Speciality Chemicals Product Application Bulletin, Powder Coatings).

There have also been known for some time, however, powder coating compositions stable to outside weathering that are based on a TGIC-free, solid mixture of epoxy resins as hardener (see, e.g., EP-A-0 536 085), where substantial amounts of a liquid, higher-functional epoxy resin, e.g. Trimellitic acid triglycidyl ester, are incorporated into a solid epoxy resin, e.g. diglycidyl terephthalate, without the total mixture of epoxy resins taking on a liquid consistency as a result. In industrial practice, however, virtually the only solid resins available hitherto for such hardener mixtures have been difunctional glycidyl esters. Furthermore, the solid resin makes up the majority of such a mixture, so that a significant disadvantage of such hardener mixtures is that their epoxy functionality is appreciably reduced in comparison with TGIC. In addition, clean glycidylisation of 1,2-dicarboxylic acids is not easy on an industrial scale.

Accordingly there is still a need for new powder coating compositions with properties comparable to those of the above-mentioned powder coating compositions from a surface-coating technology standpoint, that is to say, for powder coating compositions that, especially, have good flow behaviour and high reactivity and with which it is possible to produce coatings having a high crosslinking density and a high level of stability towards weathering and UV. The present invention provides such new powder coating compositions.

The invention relates especially to powder coating compositions that comprise a binder selected from carboxyl-group-containing polyesters, carboxyl-group-containing poly(meth)acrylates and mixtures of the said substances, and one or more epoxy compounds, wherein the epoxy compounds comprise at least one compound of formula (I) that is solid at 25° C.:

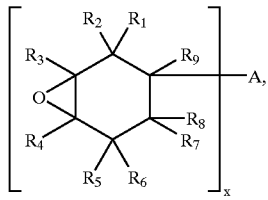

wherein

A corresponds to a group of formula (II), (III), (IV) or (VI):

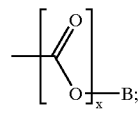

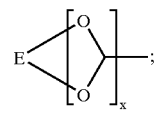

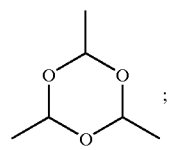

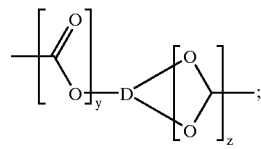

in which

B is an x-valent organic radical that is derived from a polyol having x or more hydroxyl groups by the removal of x hydroxyl groups;

E is a (2x)-valent organic radical that is derived from a polyol having (2x) or more hydroxyl groups by the removal of (2x) hydroxyl groups; and D is a (y+2z)-valent radical that is derived from a polyol having (y+2z) or more hydroxyl groups by the removal of (y+2z) hydroxyl groups;

$R_1$ and $R_5$ are each independently of the other hydrogen, halogen, $C_1$–$C_4$alkyl or $C_1$–$C_4$alkoxy or are together a methylene group; and $R_2$, $R_3$, $R_4$, $R_6$, $R_7$, $R_8$ and $R_9$ are each independently of the others hydrogen, halogen, $C_1$–$C_4$alkyl or $C_1$–$C_4$alkoxy; and x is an integer of at least 3;

y is an integer from 1 to (x−1) and z is (x−y).

The powder coating compositions according to the present invention are distinguished, inter alia, by a very good flow behaviour, and yield a cured material that has a high crosslinking density, a high degree of fastness to weathering and a high gloss. Epoxy resins of formula (I) are, in addition, toxicologically less harmful than glycidyl compounds such as are normally used for powder coating compositions.

When one of the radicals $R_1$, $R_2$, $R_3$, $R_4$, $R_5$, $R_6$, $R_7$, $R_8$ and $R_9$ in formula (I) is halogen, it is preferably, for example, chlorine or bromine; when one of those radicals is $C_1$–$C_4$alkyl or $C_1$–$C_4$alkoxy, it is, for example, methyl, ethyl, n-propyl, isopropyl, n-butyl, isobutyl or tert-butyl or an alkoxy group corresponding to one of those alkyl groups.

Preferably, the radicals $R_1$, $R_2$, $R_3$, $R_4$, $R_5$, $R_6$, $R_7$, $R_8$ and $R_9$ are $C_1$–$C_4$alkyl or, especially, hydrogen.

At least some of the compounds of formula (I) are known or are obtainable in known manner or in a manner analogous thereto.

Compounds of formula (I) wherein A corresponds to a group of formula (II) can be obtained, for example, from a polyol of formula $B(OH)_x$ wherein x is as defined hereinbefore, by esterifying the x hydroxyl groups of the polyol with cyclohexene-3-carboxylic acid and then epoxidising the carbon double bonds of the resulting polyester compound in customary manner, for example by means of an organic peracid, such as, for example, peracetic acid.

An especially preferred process for the preparation of compounds of formula (I) wherein A corresponds to a group of formula (II) comprises the transesterification of a cyclohexene-3-carboxylic acid ester, especially a cyclohexene-3-carboxylic acid $C_1$–$C_4$alkyl ester, such as methyl 3-cyclohexenecarboxylate, with a polyol of formula $B(OH)_x$, wherein x is as defined hereinbefore, in the presence of $LiNH_2$ as transesterification catalyst, and with continuous removal from the reaction mixture of the alcohol freed from the cyclohexene-3-carboxylic acid ester, the transesterification being followed by the epoxidation of the carbon double bonds of the resulting transesterification product, which is carried out in customary manner, for example by means of an organic peracid, such as, for example, peracetic acid. The use of $LiNH_2$ as catalyst results, inter alia, in especially good yields and a high degree of product purity. The said process can also be used for epoxy compounds of formula (I) wherein A corresponds to a group of formula (II) and x is 1 or 2, and the present invention relates also thereto.

Compounds of formula (I) wherein A corresponds to a group of formula (III) can be prepared, for example, in accordance with British Patent No. 870 696, by reacting a polyol of formula $B(OH)_x$, wherein x is as defined hereinbefore, with an aldehyde of formula (V)

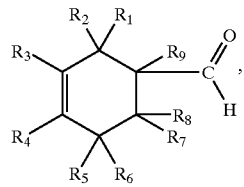

(V)

wherein $R_1$ and $R_5$, as well as $R_2$, $R_3$, $R_4$, $R_6$, $R_7$, $R_8$ and $R_9$, are likewise as defined hereinbefore, in the presence of a suitable catalyst, such as, for example, p-toluenesulfonic acid, and epoxidising the carbon double bonds of the resulting product in customary manner, for example by means of an organic peracid.

Compounds of formula (I) wherein A corresponds to a group of formula (IV) can be obtained, for example, in accordance with SU-A-1 792 956, by trimerising an aldehyde of the above-mentioned formula (V) in the presence of an acid, for example phosphoric acid or nitric acid, and epoxidising the double bonds of the resulting product, again in customary manner.

Compounds of formula (I) wherein A corresponds to a group of formula (VI) are likewise known, for example from Batog, A. E.; Pet'ko, I. P.; Kozlova, L. V.; Pandazi, I. F.; Plast. Massy (1979); (10), p. 9–10, where, for example, a compound of the above-mentioned formula (I) is described in which A corresponds to the group set out below and D is a tetravalent radical derived from pentaerythritol by the removal of 4 hydroxyl groups:

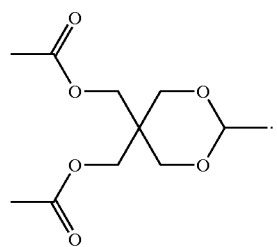

Preference is given to powder coating compositions according to the invention wherein A corresponds to a group of formula (II), especially where x is from 3 to 6 and, preferably, is 4.

B in formula (II) is preferably a radical that is derived from an aliphatic polyol having from 3 to 20 carbon atoms, from a cycloaliphatic polyol having from 5 to 20 carbon atoms or from a mixed aliphatic-cycloaliphatic polyol having from 7 to 20 carbon atoms.

More especially, the radical B in formula (II) is derived from 1,3-dihydroxy-2,2-di(hydroxymethyl)propane (pentaerythritol).

Preference is given also to powder coating compositions according to the invention wherein A corresponds to a group of formula (III), especially where x is from 3 to 6 and, preferably, is 3.

E in formula (III) and D in formula (VI) are each preferably a radical derived from an aliphatic polyol having from 3 to 20 carbon atoms, preferably 5 or 6 carbon atoms.

The radical B in formula (III) is derived especially preferably from a polyol selected from mannitol, especially D-mannitol, sorbitol, especially D-sorbitol, and dulcitol.

Powder coating compositions wherein A corresponds to a group of formula (IV) also constitute a preferred embodiment of the invention.

Another special embodiment of the powder coating compositions according to the invention is one which comprises at least one further epoxy compound of formula (I) that is solid at 25° C. wherein A corresponds to a group of formula (II) or (III) and x is 2.

For the radicals $R_1$ to $R_9$, and also for the groups B and E, the same applies in the case of epoxy compounds of formula (I) in which x is 2 as in the case of the other epoxy compounds of formula (I), in so far as the meanings are compatible with the value x=2. Examples of epoxy compounds of formula (I) wherein x is 2 that are suitable in accordance with the invention include, inter alia:

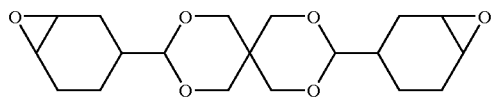

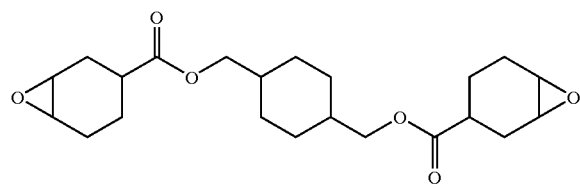

-continued

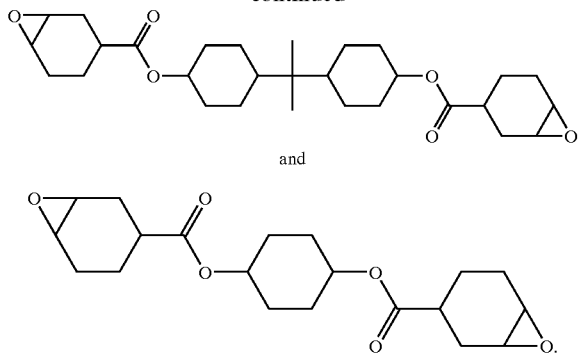

The preparation of such difunctional epoxy compounds can likewise be carried out in the manner already described above for the corresponding trifunctional and higher-functional compounds.

The epoxy compounds of formula (I) wherein x is at least 3 and the epoxy compounds of formula (I) wherein x is 2 can be present in the powder coating compositions in a widely variable molar ratio, for example in a molar ratio of up to a maximum of 1:2, preferably up to a maximum of 1:1, especially a maximum of 1:0.5.

The powder coating compositions according to the invention may in principle also comprise, in addition to the epoxy compounds of formula (I), certain amounts of one or more other epoxy compounds, e.g. glycidyl esters, such as those described in EP-A-536 085, EP-A-770 605 and EP-A-770 650. The expression "certain amount" is to be understood as meaning that a maximum of 60 percent, preferably a maximum of from 5 to 30 percent, of the total epoxy groups of the powder coating compositions according to the invention is provided by those other epoxy compounds. Especially preferably, however, the powder coating compositions according to the invention are substantially free of such other epoxy compounds, especially glycidyl compounds, such as TGIC, or glycidyl esters, such as diglycidyl terephthalate, or the corresponding glycidyl methacrylates or copolymers thereof. "Substantially free" means that a maximum of 10 percent, preferably a maximum of 5 percent, of the total epoxy groups of the powder coating compositions according to the invention is provided by TGIC or glycidyl esters. Finally, most preferred are powder coating compositions according to the invention that are completely free of glycidyl compounds, especially free of TGIC and glycidyl esters.

Suitable binders for the powder coating compositions according to the invention include, for example, free-carboxyl-group-containing polyesters having an acid number of from 10 to 160 mg, preferably from 10 to 70 mg, especially from 20 to 40 mg, of KOH per kilogram of polyester.

The polyesters are furthermore advantageously solid at room temperature (from 15 to 35° C.) and have, for example, a molecular weight (number average Mn) of from 1000 to 10 000. The ratio of Mw (weight average of the molecular weight) to Mn of those polyesters is generally from 2 to 10. There are especially suitable, for example, free-carboxyl-group-containing polyesters having a molecular weight (weight average Mw from GPC measurement using polystyrene calibration) of from 4000 to 15000, especially from 6500 to 11000, and a glass transition temperature (Tg) of from 35 to 120° C., preferably from 50 to 90° C.

Polyesters such as those mentioned are described, for example, in U.S. Pat. No. 3 397 254 and EP-A-0 600 546.

Polyesters suitable for the present invention are condensation products of difunctional, trifunctional and/or polyfunctional alcohols (polyols) with dicarboxylic acids and, optionally, trifunctional and/or polyfunctional carboxylic acids, or with corresponding carboxylic acid anhydrides. The polyols used include, for example, ethylene glycol, diethylene glycol, the propylene glycols, butylene glycol, 1,3-butanediol, 1,4-butanediol, neopentanediol, isopentyl glycol, 1,6-hexanediol, glycerol, hexanetriol, trimethylolethane, trimethylolpropane, erythritol, pentaerythritol, cyclohexanediol and 1,4-dimethylolcyclohexane. Suitable dicarboxylic acids include, for example, isophthalic acid, terephthalic acid, phthalic acid, methyl-substituted derivatives of the said acids, tetrahydrophthalic acid, methyltetrahydrophthalic acids, for example 4-methyltetrahydrophthalic acid, cyclohexane-dicarboxylic acids, succinic acid, glutaric acid, adipic acid, pimelic acid, suberic acid, azelaic acid, sebacic acid, dodecanedicarboxylic acid, fumaric acid, maleic acid and 4,4'-diphenyl-dicarboxylic acid etc.. Suitable tricarboxylic acids include, for example, aliphatic tricarboxylic acids, such as 1,2,3-propanetricarboxylic acid, aromatic tricarboxylic acids, such as trimesic acid, trimellitic acid and hemimellitic acid, and cycloaliphatic tricarboxylic acids, such as 6-methylcyclohex-4-ene-1,2,3-tricarboxylic acid. Suitable tetracarboxylic acids include, for example, pyromellitic acid and benzophenone-3,3',4,4'-tetracarboxylic acid. Commercially available polyesters especially are very commonly based on neopentyl glycol and/or trimethylolpropane as the main alcoholic monomer constituent(s) and on adipic acid and/or terephthalic acid and/or isophthalic acid and/or trimellitic acid as the main acidic monomer component(s).

Also suitable as binders are carboxyl-group-containing poly(meth)acrylates, which can be prepared in known manner by the copolymerisation of acrylic and/or methacrylic monomers, for example, $C_1$–$C_{12}$alkyl(meth)acrylates, such as methyl, ethyl, propyl, butyl, pentyl, hexyl, octyl, 2-ethylhexyl, decyl and dodecyl(meth)acrylates, $C_1$–$C_4$alkyl (meth)acrylates being preferred, or (meth)acrylamide with acrylic acid and/or methacrylic acid and, where appropriate, other ethylenically unsaturated comonomers, such as vinyl aromatic compounds, e.g. styrene, α-methylstyrene, vinyltoluene or also β-halogenated styrenes, in addition. The copolymerisation can be carried out in known manner. For example, the monomers can be dissolved in suitable organic solvents and thermally reacted in the presence of a suitable initiator that is soluble in the solvent, such as dicumyl peroxide, and in the presence of a suitable chain-transfer reagent, such as thioglycolic acid (solution polymerisation), or the monomer mixture can be suspended in water together with a solution of the initiator in an organic solvent and polymerised, or the monomer mixture can also be emulsified in water with the aid of surfactants, e.g. sodium lauryl sulfate, and reacted in the presence of a water-soluble polymerisation initiator, such as $K_2S_2O_8$ (emulsion polymerisation). The prepared poly(meth)acrylic resin is in each case then isolated in solid form from the solvent or water. The reaction can also be carried out without using solvents or water, for example according to JP-A-Sho 53-140 395. Suitable poly(meth)acrylic resins are solid at temperatures in the region of room temperature (from 15 to 25° C.). They generally have a molecular weight of from 1000 to 50000 (weight average $M_w$), preferably from 5000 to 20000.

The Tg value (glass transition temperature) of the poly (meth)acrylates, determined by DSC (heating rate 10° C./minute), is preferably from 40 to 75° C. The acid number of the resins, quoted in mg equivalent KOH per g of (meth)acrylate resin, is preferably from 20 to 160, especially from 20 to 80.

In certain cases it may also be advantageous to use, as binders, a mixture of free-carboxyl-group-containing polyesters and free-carboxyl-group-containing poly(meth) acrylates.

The powder coating compositions according to the invention comprise epoxy compounds and binders preferably in such an amount that the ratio of epoxy groups to carboxyl groups of the binder is from 2:1 to 0.5:1, preferably from 1.3:1 to 0.7:1. The compositions according to the invention may especially have a slight molar excess of epoxy groups. The molar ratio of epoxy groups to carboxyl groups in the compositions is thus preferably from 1.3:1 to 1:1, e.g. approximately from 1.2:1 to 1.1:1.

Preferably, the powder coating compositions according to the invention also comprise a catalyst for the reaction of epoxy groups with carboxyl groups. Such a catalyst is commonly an organic amine or a derivative of an amine, especially a tertiary amine or a nitrogen-containing heterocyclic compound. Preferred catalysts for the reaction of epoxy groups with carboxyl groups are phenylimidazole, N-benzyldimethylamine and 1,8-diazabicyclo[5.4.0]-7-undecene, optionally on a silicate support or triphenylphosphine, alkyltriphenylphosphonium halide, Actirone® NXJ-60 (2-propylimidazole), Actiron® NXJ-60 P (60% by weight of 2-propylimidazole on 40 % by weight of solid support), Beschleuniger® DT 3126 (alkylammonium salt in polyester). The catalyst or a catalyst mixture is preferably added in such an amount that the gel time of the mixture at 180° C. (determined according to DIN 55990) is approximately from 70 to 400 seconds, preferably from 90 to 300 seconds. Generally, approximately from 0.1 to 10 percent by weight, especially from 0.5 to 5 percent by weight, of catalyst will be required for that purpose. Of course some commercially available polyesters that can be used as binders for the powder coating compositions according to the invention will already contain a certain amount of one of the above-mentioned catalysts or of a comparable catalyst, and that amount should be taken into account in the above percentage by weight figure for the catalyst; the mentioned preferred gel times can be used to provide an indication of how much catalyst still needs to be added.

The powder coating compositions according to the invention may also comprise further additives customary in the surface-coating industry, for example light stabilizers, dyes, pigments, for example titanium dioxide pigment, degassing agents, for example benzoin, and/or flow agents. Suitable flow agents include, for example, polyvinyl acetals, such as polyvinyl butyral, polyethylene glycol, polyvinylpyrrolidone, glycerol and acrylic mixed polymers, such as, for example, those available under the names Modaflow® and Acrylron®.

Powder coating compositions according to the invention can be prepared simply by mixing the constituents together, for example in a ball mill. Another, more preferred possibility comprises melting together, blending and homogenising the constituents, preferably using an extrusion machine, such as a Buss co-kneader, and cooling and comminuting the resulting mass. In that procedure, the fact that either immediately after extrusion, or at least after they have been left to stand for a few hours, for example from 24 to 48 hours, the powder coating compositions according to the invention become so hard and brittle that they can readily be ground, has proved especially advantageous. The powder coating composition mixtures preferably have a particle size in the range from 0.015 to 500 μm, especially from 10 to 75 μm. In some cases it may also be advantageous first of all to prepare a masterbatch from portions of the binder, the epoxy resins and, optionally, further components, the masterbatch then being mixed and homogenised in a second step with the remainder of the binder and the remaining constituents to yield the finished powder coating composition.

After application to the article to be coated, the powder coating compositions are cured at a temperature of at least approximately 100° C., for example from 150 to 250° C. Curing generally takes approximately from 10 to 60 minutes. All materials that are stable at the temperatures required for the curing, especially ceramics and metals, are suitable for coating. The substrate may already have one or more base surface-coatings that are compatible with the powder coating composition.

The powder coating compositions exhibit good flow behaviour combined with good mechanical properties, good weather resistance and good resistance to chemicals.

EXAMPLE 1a
(Reaction of D-mannitol with 1,2,3,6-tetrahydrobenzaldehyde)

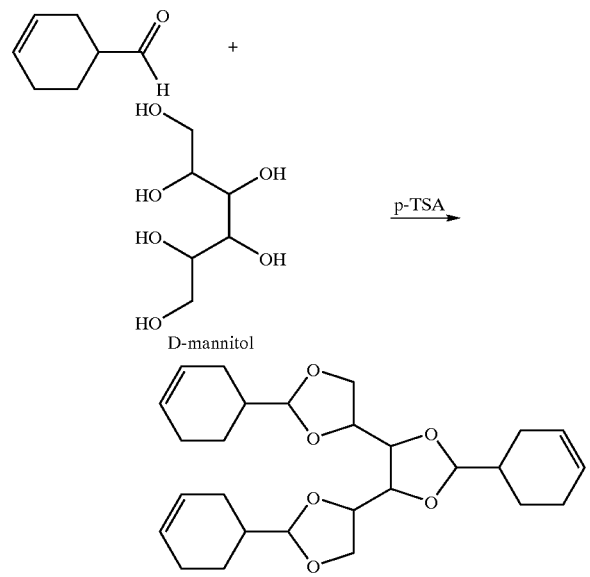

A mixture of D-mannitol (182.18 g, 1.0 mol), 1,2,3,6-tetrahydrobenzaldehyde (800 ml, 7.0 mol) and p-toluenesulfonic acid monohydrate (1.9 g, 10 mmol, p-TSA) is heated under reflux (100° C./200 mbar) and water is continuously removed azeotropically. The theoretically calculated amount of water (53 ml) is collected in the course of 2 hours, and the mixture is subsequently cooled to room temperature. The mixture is then filtered through Dowex (Fluka 44340). The removal of excess 1,2,3,6-tetrahydrobenzaldehyde yields 460.5 g (100%) of the desired product in the form of a viscous oil.

EXAMPLE 1b
(Reaction of D-sorbitol with 1,2,3,6-tetrahydrobenzaldehyde)

In the same manner as that described in Example 1a, D-sorbitol (54.50 g, 0.30 mol) and 1,2,3,6-tetrahydrobenzaldehyde (250 ml, 2.2 mol) are reacted in the presence of p-toluenesulfonic acid monohydrate (0.57 g, 3 mmol), yielding 119.0 g (87%) of the corresponding product, likewise in the form of a viscous oil.

EXAMPLE 1c (Trimerisation of 1,2,3,6-tetrahydrobenzaldehyde)

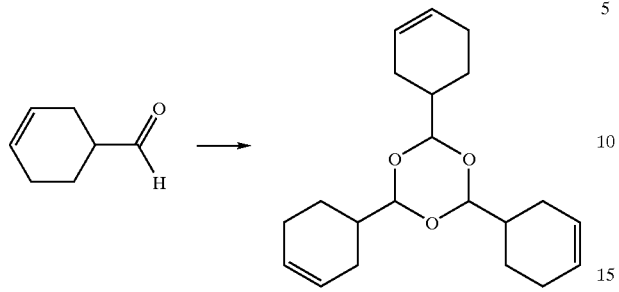

1,2,3,6-Tetrahydrobenzaldehyde (200 g, 1.8 mol) is introduced into a reactor. With vigorous stirring, orthophosphoric acid is added dropwise, the temperature being maintained at 20° C. After reaction for 25 minutes, the entire mixture forms a solid mass and 500 ml of water are added. The solid residue is washed five times with 800 ml of water each time, then washed with 500 ml of NaHCO$_3$ solution (5% in water), then washed twice with 800 ml of water each time again, and finally washed twice with 800 ml of ethanol each time. The precipitate is filtered off and dried overnight at 60° C. 162.8 g (81%) of a white powder having a melting point of 170° C. are obtained.

EXAMPLE 1d (Reaction of Pentaerythritol with 1,2,3,6-tetrahydrobenzaldehyde)

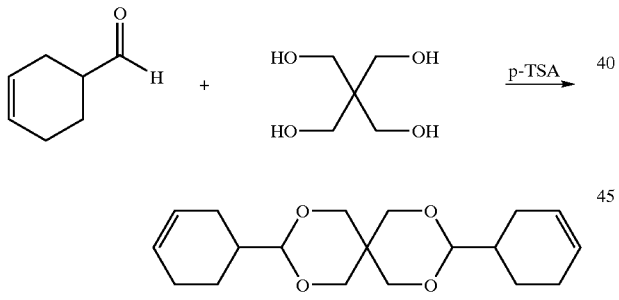

A mixture of pentaerythritol (81.76 g, 0.60 mol), 1,2,3,6-tetrahydrobenzaldehyde (250 ml, 3.5 mol) and p-toluenesulfonic acid monohydrate (1.14 g, 6 mmol, p-TSA) is heated under reflux (100° C./500 mbar) and water is continuously removed azeotropically. 17 ml of water are collected in the course of 2.5 hours, and the mixture is subsequently cooled to room temperature. The mixture is then diluted with 300 ml of ethyl acetate and washed first with 250 ml of NaHCO$_3$ solution (5% in water) and then twice with 250 ml of saturated NaCl solution. The organic layer is removed and dried over MgSO$_4$. After removal of the solvent, the mixture that remains is shaken in 1.5 liters of cold ethanol, and the precipitate that forms is filtered off, washed with ethanol and dried overnight at 70° C. 110.3 g (57%) of the desired product are obtained in the form of a yellow powder having a melting point of 97° C.

EXAMPLE 2a (Epoxidation of the Product of Example 1a)

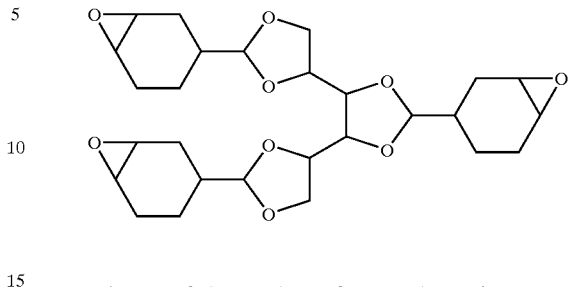

A mixture of the product of Example 1a (114.6 g, 0.25 mol) in 750 ml of dichloromethane is cooled to 10° C. A solution of peracetic acid (39% in acetic acid, 172 g, 0.88 mol) and anhydrous sodium acetate (8.79 g, 0.11 mol) is added dropwise to the mixture in the course of 1 hour. During the addition, the temperature is maintained below 30° C. The mixture is then reacted for 3 hours at room temperature. The mixture is washed with 500 ml of water, 500 ml of NaOH solution (1N) and with 500 ml of saturated NaCl solution. The organic phase is removed, stirred with sodium sulfite and dried over MgSO$_4$. Removal of the solvent yields 122.8 g (97%) of the product in the form of a viscous yellow resin (epoxy value: 5.46 eq./kg).

EXAMPLE 2b (Epoxidation of the Product of Example 1b)

The product of Example 1b (101 g, 0.22 mol), peracetic acid (39%, 151.4 g, 0.78 mol), sodium acetate (7.72 g, 94 mmol) and dichloromethane (500 ml) are reacted in the same manner as that described in Example 2a, and yield 98.0 g (88%) of the corresponding end product in the form of a viscous oil (epoxy value: 5.53 eq./kg).

EXAMPLE 2c (Epoxidation of the Product of Example 1c)

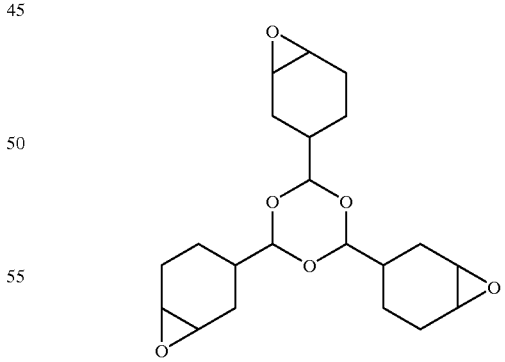

The product of Example 1c (99.1 g, 0.30 mol), peracetic acid (39%, 207.1 g, 1.06 mol), sodium acetate (10.61 g, 129 mmol) and dichloromethane (1000 ml) are reacted in the same manner as that described in Example 2a, and yield 106.1 g (94%) of the corresponding end product in the form of a white powder having a melting point of 201° C. (epoxy value: 7.55 eq./kg).

EXAMPLE 2e (Epoxidation of a Mixture of the Products of Examples 1b and 1c in a Molar Ratio of 1:1)

The product of Example 1b (114.7 g, 0.25 mol) and the product of Example 1c (82.6 g, 0.25 mol), peracetic acid (39%, 343.8 g, 1.76 mol), sodium acetate (17.36 g, 212 mmol) and dichloromethane (1000 ml) are reacted in the same manner as that described in Example 2a, and yield 215.8 g (97%) of the corresponding mixture of epoxy compounds of formula (I) in the form of a yellow powder (epoxy value: 6.08 eq./kg).

EXAMPLE 2f (Epoxidation of a Mixture of the Products of Examples 1a and 1c in a Molar Ratio of 42:58)

The product of Example 1a (33.0 g, 72 mmol) and the product of Example 1c (33.0 g, 100 mmol), peracetic acid (39%, 118.0 g, 607 mmol), sodium acetate (6.03 g, 73 mmol) and dichloromethane (500 ml) are reacted in the same manner as that described in Example 2a, and yield 69.1 g (97%) of the corresponding mixture of epoxy compounds of formula (I) in the form of a white powder (epoxy value: 6.55 eq./kg).

EXAMPLE 2g (Epoxidation of a Mixture of the Products of Examples 1c and 1d in a Molar Ratio of Approximately 1:1)

The product of Example 1c (50.0 g, 156 mmol) and the product of Example 1d (50.0 g, 151 mmol), peracetic acid (39%, 196.1 g, 1.0 mol), sodium acetate (10.0 g, 122 mmol) and dichloromethane (800 ml) are reacted in the same manner as that described in Example 2a, and yield 98.4 g (87%) of the corresponding mixture of epoxy compounds of formula (I) in the form of a white powder (epoxy value: 5.72 eq./kg).

EXAMPLE 3

The powder coating composition indicated in the following Table 3/1 is homogenised using an extruder (laboratory extruder from PRISM, The Old Stables, England). The cooled extrudate is ground to give the finished powder coating composition having a particle size of approximately 40 micrometers.

TABLE 3/1

Powder coating composition formulation

| Formulation | A [g] |
|---|---|
| Uralac P 3485[1] | 60.00 |
| Epoxy compound according to Example 2a | 5.80 |
| Benzoin | 0.20 |
| Acrylron[2] | 1.00 |
| TiO$_2$ [Cronos 2160] | 33.00 |

[1]Polyester based on terephthalic acid, isophthalic acid and neopentyl glycol having an acid number of 28 and a glass transition temperature Tg of 71° C.;
[2]Acrylic mixed polymer as flow agent.

Using an electrostatic spray gun, the powder coating composition is applied to a Q panel as substrate. The coated panel is then placed in an oven in order to melt and fully cure the powder coating composition. The gel time, the curing temperature and the curing time, and also the thickness of the resulting powder resin coating, are indicated in the following Table 3/2 together with properties of the resulting coatings that are important from the standpoint of surface-coating technology.

TABLE 3/2

| Property | A |
|---|---|
| Gel time 180° C. [sec.] | 210 |
| Full cure | 15 min./200° C. |
| Layer thickness [mm] | 55 |
| Substrate | Q panel |
| Gloss 60° | 94 |
| Gloss 20° | 84 |
| Yellowness value Yi | 4.8 |
| Flow [rating][3] | 12 |
| Acetone test[5], 1 min. [rating] | 3 |

[3]Empirical scale from 0 (very good) to 18 (orange-peel)
[5]According to DIN 53320. The specimen is kept in acetone for 1 minute. The result is evaluated in accordance with the following scale of five ratings: 0 = unchanged; 1 = resistant, cannot be scratched with a finger nail; 2 = difficult to scratch, may stain cottonwool pad; 3 = softened, easily scratchable; 4 = beginning to separate or dissolve; 5 = complete dissolution.

EXAMPLE 4

The powder coating compositions indicated in the following Table 4/1 are homogenised using an extruder (laboratory extruder from PRISM, The Old Stables, England). The total amount of powder coating composition in each case is approximately from 100 to 200 grams. The cooled extrudates are ground to give the finished powder coating composition having a particle size of approximately 40 mm.

TABLE 4/1

Powder coating composition formulations

| Formulation | B [g] | C [g] | D [g] | E [g] |
|---|---|---|---|---|
| Uralac P 3485[1] | 59.05 | 58.11 | 58.71 | 59.17 |
| DGT[6] | — | 1.80 | 4.37 | 4.41 |
| Epoxy compound according to Example 2b | 5.92 | 4.56 | 1.38 | 1.39 |
| DT 3126[7] | — | 0.50 | 0.50 | — |
| Benzoin | 0.20 | 0.20 | 0.20 | 0.20 |
| Acrylron[2] | 1.50 | 1.50 | 1.50 | 1.50 |
| TiO$_2$ [Cronos 2160] | 33.33 | 33.33 | 33.33 | 33.33 |

[6]Diglycidyl terephthalate
[7]Alkylammonium salt in polyester

The properties found for the coatings are indicated in the following Table 4/2.

TABLE 4/2

| Property | B | C | D | E |
|---|---|---|---|---|
| Gel time @ 180° C. [sec.] | 165 | 265 | 400 | 530 |
| Full cure | 15 min./180° C. | 15 min./200° C. | 15 min./200° C. | 15 min./200° C. |
| Layer thickness [mm] | 54 | 55 | 56 | 55 |
| Substrate | Q panel | Q panel | Q panel | Q panel |
| Gloss 60° | 95 | 95 | 96 | 96 |
| Gloss 20° | 84 | 84 | 88 | 88 |
| Yellowness value Yi | 2.7 | 4.8 | 1.7 | 0.3 |
| Flow[3] [rating] | 10 | 10 | 10 | 6 |
| Acetone test[5], 1 min. [rating] | 3 | 3 | 3 | 4 |

EXAMPLE 5

The powder coating compositions indicated in Table 5/1 are prepared in accordance with Example 4.

TABLE 5/1

Powder coating composition formulations

| Formulation | F [g] | G [g] | H [g] |
|---|---|---|---|
| Uralac P 3485[1)] | 58.38 | 59.91 | 59.91 |
| Epoxy compound according to Example 2c | 4.59 | 4.89 | 4.89 |
| DT 3126[7)] | 2.00 | — | — |
| Benzoin | 0.20 | 0.20 | 0.20 |
| Crylcoat 164[9)] | — | 1.00 | — |
| Acrylron[2)] | 1.50 | 1.00 | 1.00 |
| TiO$_2$ [Cronos 2160] | 33.33 | 33.00 | 33.00 |

[9)]Alkyltriphenylphosphonium bromide in polyester

The properties found for the coatings are indicated in the following Table 5/2.

TABLE 5/2

| Property | F | G | H |
|---|---|---|---|
| Gel time @ 180° C. [sec.] | 150 | 160 s | 90 |
| Full cure | 15 min./180° C. | 15 min./200° C. | 15 min./200° C. |
| Layer thickness [mm] | 53 | 48 | 51 |
| Substrate | Q panel | Q panel | Q panel |
| Gloss 60° | — | 95 | 95 |
| Gloss 20° | — | 83 | 71 |
| Yellowness value Yi | — | 2.4 | 0.0 |
| Flow [rating][3)] | 8 | 10 | 10 |
| Acetone test[5)], 1 min. [rating] | 3 | 3 | 3 |

EXAMPLE 6

The powder coating composition indicated in Table 6/1 is prepared in accordance with Example 4.

TABLE 6/1

Powder coating composition formulation

| Formulation | I [g] |
|---|---|
| Uralac P 3485[1)] | 59.54 |
| Epoxy compound according to Example 2e | 5.43 |
| Benzoin | 0.20 |
| Acrylron | 1.50 |
| TiO$_2$ [Cronos 2160] | 33.33 |

The properties found for the corresponding coating are indicated in the following Table 6/2.

TABLE 6/2

| Property | I |
|---|---|
| Gel time 180° C. [sec.] | 285 |
| Full cure | 15 min./180° C. |
| Layer thickness [mm] | 86 |
| Substrate | Q panel |
| Gloss 60° | 91 |
| Gloss 20° | 75 |
| Yellowness value Yi | 3.3 |
| Flow [rating][3)] | 10–12 |
| Acetone test,[5)] 1 min. [rating] | 2 |

EXAMPLE 7

The powder coating compositions indicated in Table 7/1 are prepared in accordance with Example 4.

TABLE 7/1

Powder coating composition formulations

| Formulation | J [g] | K [g] |
|---|---|---|
| Uralac P 3485[1)] | 60.66 | 59.79 |
| Epoxy resin according to Example 2f | 5.14 | 6.01 |
| Benzoin | 0.20 | 0.20 |
| Acrylron[2)] | 1.00 | 1.00 |
| TiO$_2$ [Cronos 2160] | 33.00 | 33.33 |

The properties found for the corresponding coating are indicated in the following Table 7/2.

TABLE 7/2

| Property | J | K |
|---|---|---|
| Gel time @ 180° C. [sec.] | 200 | 200 |
| Full cure | 15 min./200° C. | 15 min./200° C. |
| Layer thickness [mm] | 45 | 89 |
| Substrate | Q panel | Q panel |
| Gloss 60° | 95 | 96 |
| Gloss 20° | 82 | 77 |
| Yellowness value Yi | 2.0 | 7.9 |
| Flow[3)] [rating] | 10 | 6–8 |
| Acetone test[5)], 1 min. [rating] | 3 | 3 |

EXAMPLE 8

The powder coating compositions indicated in Table 8/1 are prepared in accordance with Example 4.

TABLE 8/1

Powder coating composition formulations

| Formulation | L [g] | M [g] |
|---|---|---|
| Uralac P 3485[1)] | 91.27 | 60.78 |
| Epoxy compound according to Example 2e | 7.53 | 5.02 |
| Benzoin | 0.20 | 0.20 |
| Acrylron[2)] | 1.00 | 1.00 |
| TiO$_2$ [Cronos 2160] | — | 33.00 |

The properties found for the corresponding coatings are indicated in the following Table 8/2.

TABLE 8/2

| | L | M |
|---|---|---|
| Gel time @ 180° C. [sec.] | 180 | 180 |
| Full cure | 15 min./200° C. | 15 min./200° C. |
| Layer thickness [mm] | 55 | 55 |
| Substrate | Q panel | Q panel |
| Gloss 60° | 108 | 96 |
| Gloss 20° | 76 | 81 |
| Yellowness value Yi | — | 6.8 |
| Flow[3)] [rating] | 2 | 6–8 |
| Acetone test[5)], 1 min. [rating] | 3 | 3 |

EXAMPLE 9

Preparation of an Epoxy Compound of the Following Formula

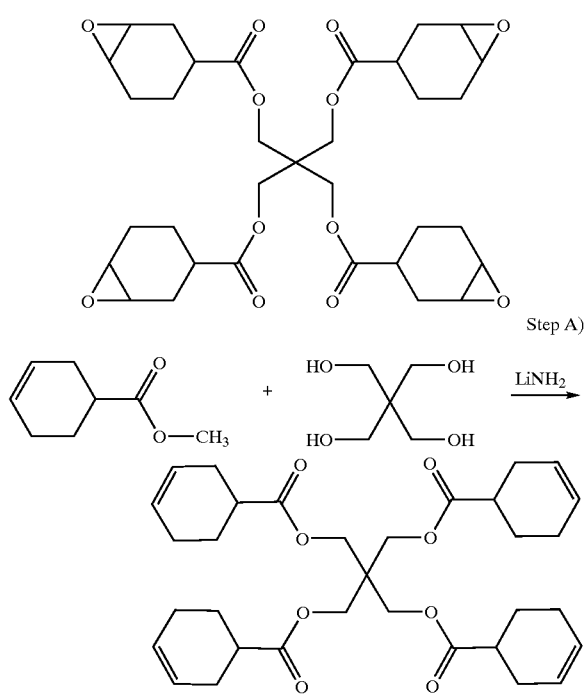

Step A)

100 ml of xylene (purissimum, stored over a 4A molecular sieve, water content <0.02%), 146.3 g (1.04 mol) of methyl 3-cyclohexenecarboxylate and 27.1 g (0.20 mol) of pentaerythritol are introduced into a well-insulated reaction vessel equipped with a thermometer, a mechanical stirrer and a distillation bridge. The resulting suspension is heated at a temperature of from 145 to 150° C. for 30 minutes under nitrogen and with stirring, further xylene gradually being added to the reaction vessel at the same rate as that at which xylene is distilled off. 0.23 g (0.01 mol) of $LiNH_2$ is then added. After approximately 30 minutes the methanol begins to distill off. The total distillation time is approximately 6 hours, during the course of which 150 ml of xylene are added. The reaction vessel is then cooled to room temperature. The reaction mixture is diluted with 200 ml of toluene and washed with 200 ml of water. The organic phase is dried over $MgSO_4$ and filtered. The solvent and excess methyl 3-cyclohexenecarboxylate are then removed using a rotary evaporator (120° C./5 mbar). 110 g (97% yield) of reaction product are obtained in the form of a colourless, viscous liquid, which crystallises on being left to stand. The melting point of the crystallisate is 65° C.

Step B)

A mixture of 90.0 g (0.16 mol) of the reaction product obtained according to Step A in 700 ml of dichloromethane is cooled to a temperature of 10° C., and a suspension of 148 g (0.76 mol, 39% in acetic acid) of peracetic acid and 7.3 g (0.088 mol) of anhydrous sodium acetate is added dropwise thereto over a period of approximately 45 minutes. During the addition, the temperature is maintained below 30° C. The solution is subsequently allowed to react further for approximately 3 hours at room temperature (25–30° C.). The resulting reaction mixture is washed twice with 200 ml of water, then twice with 200 ml of a 5% $NaHCO_3$ solution and finally a further twice with 200 ml of water. The organic phase is subsequently stirred with sodium sulfite until a peroxide test is negative, and is subsequently dried over $MgSO_4$. After removal of the solvent a colourless, viscous liquid is obtained which slowly crystallises on being left to stand. Recrystallisation from 200 ml of MeOH yields 80 g (80% yield) of the desired product in the form of a white, crystalline powder (epoxy value: 6.1 eq./kg; melting point: 95° C.).

EXAMPLE 10

The powder coating compositions indicated in Table 10/1 are prepared in accordance with Example 4.

TABLE 10/1

Powder coating composition formulations

| Formulation | N [g] | O [g] | P [g] | Q [g] |
| --- | --- | --- | --- | --- |
| Uralac P 3485[1)] | 56.26 | 58.89 | 58.80 | 58.82 |
| DGT[6)] | — | 2.74 | — | — |
| HHDGP[10)] | — | — | — | 1.12 |
| HHDGT[11)] | — | — | 1.14 | — |
| Epoxy compound according to Example 9 | 5.71 | 2.84 | 4.53 | 4.53 |
| DT 3126[7)] | — | 0.50 | 0.50 | 0.50 |
| Benzoin | 0.20 | 0.20 | 0.20 | 0.20 |
| Acrylron[2)] | 1.50 | 1.50 | 1.50 | 1.50 |
| $TiO_2$ [Cronos 2160] | 33.33 | 33.33 | 33.33 | 33.33 |

[10)]Hexahydrodiglycidyl phthalate (Araldite PY 284)
[11)]Hexahydrodiglycidyl terephthalate The properties found for the corresponding coatings are indicated in the following Table 10/2.

TABLE 10/2

| | N | O | P | Q |
| --- | --- | --- | --- | --- |
| Gel time @ 180° C. [sec.] | 190 | 280 | 195 | 195 |
| Full cure | 15 min./ 180° C. | 15 min./ 180° C. | 15 min./ 180° C. | 15 min./ 180° C. |
| Layer thickness [mm] | 62 | 48 | 58 | 60 |
| Substrate | Q panel | Q panel | Q panel | Q panel |
| Gloss 60° | 95 | 95 | 96 | 95 |
| Gloss 20° | 86 | 83 | 88 | 85 |

TABLE 10/2-continued

|  | N | O | P | Q |
|---|---|---|---|---|
| Yellowness value Yi | 0.4 | −1.3 | −0.4 | −0.6 |
| Flow[3] [rating] | 10 | 10 | 10 | 11 |
| Impact, reverse[4] [kg cm] | 100 | >160 | 140 | 120 |
| Impact, front[4] [kg cm] | 160 | >160 | 160 | 160 |
| Acetone test[5], 1 min. [rating] | 3 | 3 | 3 | 3 |

[4]The impact deformation is determined by dropping onto the coated face, from a specific height from behind (reverse side) or from the front, a punch weighing 2 kg, having a 20 mm diameter ball on its underside, with the underside leading. The value indicated is the product of the weight of the punch in kg and the test height in cm at which there is still no detectable damage to the coating.

EXAMPLE 11

The powder coating compositions indicated in Table 11/1 are prepared in accordance with Example 4.

TABLE 11

Powder coating composition formulations

| Formulation | R[g] | S[g] | T[g] | U[g] | V[g] |
|---|---|---|---|---|---|
| Uralac P 3485[1] | 58.53 | 58.21 | 58.60 | 57.99 | 58.49 |
| Epoxy compound according to Example 9 | 4.51 | 4.84 | 4.51 | 5.12 | 4.78 |
| Epoxy compound[12] | 1.43 | 1.42 | — | — | — |
| Epoxy compound[13] | — | — | 1.36 | 1.36 | — |
| Epoxy compound[14] | — | — | — | — | 1.20 |
| DT 3126[7] | 0.50 | 0.50 | 0.50 | 0.50 | 0.50 |
| Benzoin | 0.20 | 0.20 | 0.20 | 0.20 | 0.20 |
| Acrylron[2] | 1.50 | 1.50 | 1.50 | 1.50 | 1.50 |
| TiO$_2$ [Cronos 2160] | 33.33 | 33.33 | 33.33 | 33.33 | 33.33 |

12)

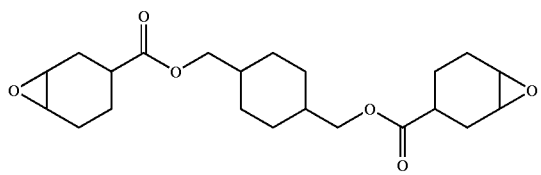

Epoxy value: 5.1 eq./kg
m.p.: 85° C.

13)

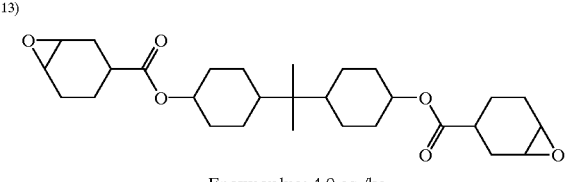

Epoxy value: 4.0 eq./kg
m.p.: 215° C.

14)

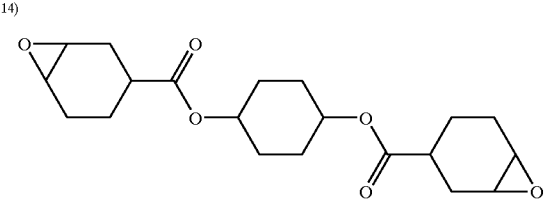

Epoxy value: 5.4 eq./kg
m.p.: 30° C. (waxy)

The above epoxy compounds 12), 13) and 14) are obtained in accordance with the same preparation procedure as in Example 9.

The properties found for the corresponding coatings are indicated in the following Table 11/2.

TABLE 11/2

|  | R | S | T | U | V |
|---|---|---|---|---|---|
| Gel time @ 180° C. [sec.] | 240 | 230 | 210 | 215 | 215 |
| Full cure | 15 min. 180° C. | 15 min. 200° C. | 15 min. 200° C. | 15 min. 200° C. | 15 min. 200° C. |
| Layer thickness [mm] | 48 | 47 | 72 | 47 | 47 |
| Substrate | Q panel | Q panel | Q panel | Q panel | Q panel |
| Gloss 60° | 91 | 94 | 94 | 94 | 95 |
| Gloss 20° | 86 | 84 | 87 | 77 | 82 |
| Yellowness value Yi | −2.3 | −2.1 | 2.0 | −2.8 | −1.9 |
| Flow[3] [rating] | 10 | 10 | 10 | 11 | 9 |
| Impact, reverse[4] [kg cm] | >160 | >160 | >160 | >160 | >160 |
| Impact, front[4] [kg cm] | >160 | >160 | >160 | >160 | >160 |
| Acetone test[5], 1 min. [rating] | 3 | 3 | 3 | 3 | 3 |

EXAMPLE 12

The powder coatings indicated in Table 12/1 are prepared in accordance with Example 4.

TABLE 12/1

Powder coating composition formulations

| Formulation | X [g] | Y [g] | Z [g] |
|---|---|---|---|
| Uralac P 3485 | 58.56 | 57.86 | 57.55 |
| Epoxy compound, prepared in accordance with Example 2b (5.60 eq./kg) | 2.90 | 2.15 | 5.13 |
| Epoxy compound[12] | 3.01 | 4.46 | — |
| Epoxy compound[13] | — | — | 1.80 |
| DT 3126[7] | 0.50 | 0.50 | 0.50 |
| Benzoin | 0.20 | 0.20 | 0.20 |
| Acrylron[2] | 1.50 | 1.50 | 1.50 |
| TiO$_2$ [Cronos 2160] | 33.33 | 33.33 | 33.33 |

[12]; [13]; [7]; [2]See corresponding definitions hereinbefore.

The properties found for the corresponding coatings are indicated in the following Table 12/2.

TABLE 12/2

|  | X | Y | Z |
|---|---|---|---|
| Gel time @ 180° C. [sec.] | 245 sec. | 410 sec. | 220 sec. |
| Full cure | 15 min./ 180° C. | 15 min./ 180° C. | 15 min./ 180° C. |
| Layer thickness [mm] | 60 | 59 | 69 |
| Substrate | Q panel | Q panel | Q panel |
| Gloss 60° | 95 | 94 | 95 |
| Gloss 20° | 88 | 86 | 86 |
| Yellowness value Yi | 4.5 | 3.3 | 5.1 |
| Flow[3] [rating] | 10 | 10 | 10 |
| Acetone test[5], 1 min. [rating] | 3 | 3 | 3 |

EXAMPLE 13

A clear powder coating composition (W) according to the invention and three clear powder coating compositions used for comparison purposes (W1, W2, W3), each based on Uralac 3489[14]) and the epoxy compounds indicated in the following Table 13/1 (molar ratio of the COOH groups of the polyester to the epoxy groups of the epoxy compound in each case 0.95 to 1) as well as 0.2 percent by weight of benzoin and 1.5 percent by weight of acrylon (all compositions without curing accelerator) are homogenised by extrusion twice using a laboratory extruder from PRISM, The Old Stables, England, (T1=30° C./T2=80° C.). The following are determined in each case: the gel time at 180° C.; the percentage of gelled material (gelled amount) in the cured composition after curing for 15 min. at 200° C., the Tg value of the cured composition and the viscosity of the cured systems at 180° C. The values are likewise indicated in Table 13/1.

TABLE 13/1

Powder coating composition formulations

| Formulation | Epoxy compound (% by wt.) | Gel time @ 180° C. [sec.] | Gelled amount[18] [% by wt.] | Tg after curing, onset [° C.] | Viscosity[19] [Pa · s] |
|---|---|---|---|---|---|
| W according to the invention | Epoxide according to Example 9 (7.8%) | 375 | 93.5 | 76 | 10700 |
| Comparison W1 | PT 910[15] (7.2%) | 450 | 80.4 | 72 | 510 |
| Comparison W2 | XB 912[16] (7.2%) | 390 | 89.0 | 73 | 2100 |
| Comparison W3 | PT 810[17] (5.2%) | 210 | 95.2 | 76 | 9050 |

[14] Uralac P3489 is a polyester based on Terephthalic acid, Isophthalic acid and Neopentylglycol with an acid value of 28 mg KOH/g and a Tg of 70° C.
[15] Araldite PT910 is a solid mixture of 75% by wt. of diglycidyl terephthalate and 25% by wt. of triglycidyl trimellitate according to US-A-5 457 168.
[16] XB 912 is a solid mixture of 60% by wt. of diglycidyl terephthalate and 40% by wt. of triglycidyl trimellitate according to US-A-5 457 168.
[17] Araldite PT810 = triglycidyl isocyanurate
[18] The gelled amount is determined as follows: A specimen, weighing 1 g, of a 50 μm thick film of the powder coating composition, which has been cured for 15 minutes at 200° C., is extracted for 2 hours three times with 50 ml of acetone each time. The value quoted corresponds to the undissolved residue that remains, quoted in percent by weight.
[19] Measurement of the (dynamic) viscosity is determined using a rheometric measuring apparatus. The specimen is subjected between two parallel plates (diameter 50 mm) to an oscillating shearing stress (1 Hz; shearing stress (strain) 15%). The viscosity is determined at 180° C. as a function of the time. The values quoted in the Table correspond to the viscosity of the cured system.

The gelled amount of the powder coating composition (W) according to the invention, which is significantly increased compared with the comparison compositions based on Araldite PT910 (Comparison W1) and XB 912 (Comparison W2), is a clear indication of the surprisingly increased crosslinking density in cured material based on the composition according to the invention under the same curing conditions (15 min./200° C.). The crosslinking density, which with the same curing time is increased, also makes clear the higher reactivity of the systems according to the invention, that reactivity being comparable with compositions based on Araldite PT810 (Comparison W3). Likewise, the viscosity of the system according to the invention after curing is significantly increased compared with all three comparison systems (W1, W2 and W3), demonstrating the comparatively high crosslinking density and reactivity of the powder coating compositions according to the invention.

What is claimed is:

1. A powder coating comprising a binder selected from carboxyl-group-containing polyesters, carboxyl-group-containing poly(meth)acrylates and mixtures of the said substances, and one or more epoxy compounds, wherein the epoxy compounds comprise at least one compound of formula (I) that is solid at 25° C.:

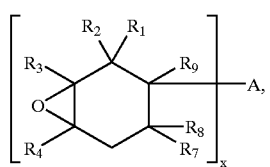

wherein
A corresponds to a group of formula (II)

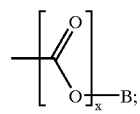

in which
B is an x-valent organic radical that is derived from a polyol having x or more hydroxyl groups by the removal of x hydroxyl groups;
$R_1$ and $R_5$ are each independently of the other hydrogen, halogen, C1–C4alkyl or C1–C4alkoxy or are together a methylene group; and
$R_2$, $R_3$, $R_4$, $R_6$, $R_7$, $R_8$ and $R_9$ are each independently of the others hydrogen, halogen, C1–C4alkyl or $C_1$–C4alkoxy; and
x is an integer of at least 3.

2. A powder coating composition according to claim 1, wherein x is from 3 to 6.

3. A powder coating composition according to claim 2, wherein B is a radical that is derived from an aliphatic polyol having from 3 to 20 carbon atoms, a cycloaliphatic polyol having from 5 to 20 carbon atoms or a mixed aliphatic-cycloaliphatic polyol having from 7 to 20 carbon atoms.

4. A powder coating composition according to claim 1, wherein the polyol is 1,3-dihydroxy-2,2-di(hydroxymethyl)propane (pentaerythritol).

5. A powder coating composition according to claim 1, which is substantially free of glycidyl compounds.

6. A powder coating composition according to claim 1, further comprising at least one epoxy compound of formula (I) that is solid at 25° C. wherein A compound to a group of formula (II) or following formula (III)

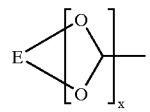

wherein E is a (2x)-valent organic radical that is derived from a polyol having (2x) or more hydroxyl groups by the removal of (2x) hydroxyl groups and x is 2.

7. A powder coating composition according to claim 6, wherein the mixture of epoxy compounds of formula (I) wherein x is at least 3 and epoxy compounds wherein x is 2, are present at a molar ratio of up to a maximum of 1:2.

8. A powder coating composition according to claim 6, wherein the mixture of epoxy compounds of formula (I) wherein x is at least 3 and epoxy compounds wherein x is 2, are present at a molar ratio of up to a maximum of 1:1.

9. A powder coating composition according to claim 1, which is substantially free of triglycidyl isoyanurate and glycidyl esters.

10. A powder coating composition according to claim 1, wherein x is 4.

* * * * *